United States Patent
Klocke et al.

(10) Patent No.: US 8,337,548 B2
(45) Date of Patent: Dec. 25, 2012

(54) IMPLANT AND SYSTEM OF AN IMPLANT AND AN EXCITATION DEVICE

(75) Inventors: Bjoern Klocke, Zurich (CH); Matthias Fringes, Ansbach (DE); Eugen Hofmann, Zurich (CH)

(73) Assignee: Biotronik vi Patent AG, Baar (CH)

( * ) Notice: Subject to any disclaimer, the term of this patent is extended or adjusted under 35 U.S.C. 154(b) by 500 days.

(21) Appl. No.: 12/171,566

(22) Filed: Jul. 11, 2008

(65) Prior Publication Data

US 2009/0017088 A1   Jan. 15, 2009

(30) Foreign Application Priority Data

Jul. 13, 2007 (DE) .................. 10 2007 032 688

(51) Int. Cl.
*A61F 2/06* (2006.01)
*A61F 2/48* (2006.01)
*A61K 9/22* (2006.01)

(52) U.S. Cl. ... 623/1.42; 623/24; 604/890.1; 604/892.1; 604/891.1

(58) Field of Classification Search .................. 623/1.42
See application file for complete search history.

(56) References Cited

U.S. PATENT DOCUMENTS

| | | | | |
|---|---|---|---|---|
| 5,029,805 A | * | 7/1991 | Albarda et al. .................. 251/11 |
| 5,161,774 A | * | 11/1992 | Engelsdorf et al. .............. 251/11 |
| 5,624,411 A | * | 4/1997 | Tuch .............................. 604/265 |
| 5,797,898 A | * | 8/1998 | Santini et al. ................ 604/890.1 |
| 5,962,081 A | * | 10/1999 | Ohman et al. .................. 427/534 |
| 6,551,838 B2 | * | 4/2003 | Santini et al. .................... 436/174 |
| 6,669,683 B2 | * | 12/2003 | Santini et al. ................ 604/890.1 |
| 6,953,455 B2 | * | 10/2005 | Cho et al. ...................... 604/890.1 |
| 7,041,130 B2 | * | 5/2006 | Santini et al. ................. 623/1.42 |
| 7,217,428 B2 | * | 5/2007 | Tuszynski et al. ............ 424/464 |
| 7,223,282 B1 | * | 5/2007 | Hossainy ..................... 623/1.15 |
| 7,604,628 B2 | * | 10/2009 | Santini et al. ................ 604/890.1 |
| 2002/0082680 A1 | * | 6/2002 | Shanley et al. ............... 623/1.16 |
| 2003/0149420 A1 | | 8/2003 | Richter |
| 2004/0030379 A1 | | 2/2004 | Hamm et al. |
| 2005/0055014 A1 | * | 3/2005 | Coppeta et al. ............ 604/890.1 |
| 2005/0149169 A1 | | 7/2005 | Wang et al. |
| 2005/0265991 A1 | | 12/2005 | Tuszynski et al. |
| 2007/0010868 A1 | | 1/2007 | Ferren et al. |

(Continued)

FOREIGN PATENT DOCUMENTS

EP    1574180 A2    9/2005

(Continued)

OTHER PUBLICATIONS

Search Report for German Patent Application No. 10 2007 032 688.4; Jun. 25, 2008.

(Continued)

*Primary Examiner* — David Isabella
*Assistant Examiner* — Jacqueline Woznicki
(74) *Attorney, Agent, or Firm* — Greer, Burns & Crain, Ltd.

(57) ABSTRACT

An implant comprising a body (1), at least one active pharmaceutical substance (4) and an element (5, 15, 35, 45, 55) deflectable in relation to the body, serving to release the at least one active pharmaceutical substance (4) during or after an external excitation of the deflection. Also disclosed is a system of such an implant and an excitation device (30, 70).

11 Claims, 3 Drawing Sheets

U.S. PATENT DOCUMENTS

2007/0149954 A1* 6/2007 Hood et al. ............. 604/891.1
2008/0033569 A1* 2/2008 Ferren et al. ............ 623/23.7

FOREIGN PATENT DOCUMENTS

| | | | |
|---|---|---|---|
| WO | 2004010971 | A1 | 2/2004 |
| WO | 2004093643 | A2 | 11/2004 |
| WO | 2005072169 | A2 | 8/2005 |
| WO | 2006029364 | A2 | 3/2006 |
| WO | 2007136923 | A1 | 11/2007 |

OTHER PUBLICATIONS

Search Report for European Patent Application No. 08158593.7; Oct. 16, 2008.

* cited by examiner

| Axes | Conversion type | Constant values |
|---|---|---|
| a) A3, A1, A2 (plate, 5) | Oscillation in thickness — Polarity ↓, Field ↕, Deformation ↕ | $d_{33}, g_{33}, k_{33}$ $s_{33}, e_{33}$ |
| | Oscillation in length ↓ ↕ ↔ | $d_{31}, g_{31}, k_{31}$ $s_{11}, e_{33}$ |
| b) A3, A1, A2 (disc, 35) | Oscillation in radial direction ↓ ↕ | $d_{31}, g_{31}, kp$ $s_{11}, e_{33}$ |
| | Oscillation in thickness ↓ ↕ | $d_{33}, g_{33}, k_{33}$ $s_{33}, e_{33}$ |
| c) A3, 45, A1, A2 (block) | Oscillation in shear force direction ↓ ↔ ↕ | $d_{15}, g_{15}, k_{15}$ $s_{44}, s_{55}, e$ |
| d) 55 (tube) | Oscillation in (wall) thickness | $d_{33}, g_{33}, k_{33}$ $s_{33}, e_{33}$ |
| | Oscillation in length / Oscillation in radial direction | $d_{31}, g_{31}, k_{31}$ $s_{11}, e_{33}$ |

Fig. 1

IMPLANT AND SYSTEM OF AN IMPLANT AND AN EXCITATION DEVICE

PRIORITY CLAIM

This patent application claims priority to German Patent Application No. 10 2007 032 688.4, filed Jul. 13, 2007, the disclosure of which is incorporated herein by reference in its entirety.

FIELD

The present disclosure relates to an implant having a body and at least one active pharmaceutical substance. The present disclosure also relates to a system with such an implant.

BACKGROUND

For purposes of the present disclosure, "implants" are understood to refer to all nonviable animal or human (xenogeneic or allogeneic) elements or artificial elements which can be introduced into a human or animal body or organism and which remain in the respective organism for at least a certain period of time. Such implants include, for example, stents, pacemakers, artificial heart valves, bone or skin replacement items and depot implants or reservoir implants which serve to release medications over a longer period of time, e.g., depot implants for treatment of cancer such as prostate cancer and biodegradable gentamicin depot implants. These implants consist of a basic body or carrier and optionally additional components. Such an additional component -often includes active pharmaceutical substances such as medicines in or on the body which are released in the body over a certain period of time.

For purposes of the present disclosure, an "active pharmaceutical substance" (or therapeutically active or effective substance) is a vegetable, animal or synthetic active ingredient (medication) or a hormone that is used in a suitable dosage as a therapeutic agent to influence states or functions of the body, as a substitute for active ingredients such as insulin which are naturally produced by the human or animal body, and for eliminating pathogens, tumors, cancer cells or exogenous substances that are rendered harmless. The release of the substance in the environment of the endoprosthesis has a positive effect on the course of healing or serves to render malignant cells harmless in oncology and/or counteracts pathological changes in tissue due to a surgical procedure.

Such active pharmaceutical substances have an anti-inflammatory, anti-proliferative and/or spasmolytic effect, which makes it possible to prevent restenoses, inflammations or (vascular) spasms, for example. In especially preferred exemplary embodiments, such substances may consist of one or more substances from the group of active ingredients consisting of calcium channel blockers, lipid regulators (such as fibrates), immunosuppressants, calcineurin inhibitors (such as tacroliumus), antiphlogistics (such as cortisone or diclofenac), anti-inflammatories (such as imidazoles), anti-allergics, oligonucleotides (such as dODN), estrogens (such as genistein), endothelium-forming agents (such as fibrin), steroids, proteins, hormones, insulins, cytostatics, peptides, vasodilators (such as sartanes) and antiproliferative substances.

Today there is often the desire for these implants that are introduced into the human or animal body to release the active pharmaceutical substances as needed at certain points in time and/or over a certain desired period of time, e.g., depending on the value of a certain bodily function, the blood pressure, and/or in a certain amount in the body, for example, into the surrounding tissue or the surrounding body fluid such as blood. It should be possible for the substance to be dispensed in a process that is controlled by the physician or patient by means of an external device or for the substance to be released automatically, e.g., depending on the values measured by a sensor system for bodily functions. By releasing the active pharmaceutical substance in this way, it is possible to avoid adverse effects for the patient because the active pharmaceutical substance is dispensed only in a desired time window. Therefore, there cannot be any underdosing or overdosing due to such a release.

Treatment of patients by means of stents is an area of applications of particular interest. Stents are endovascular prostheses which can be used for treatment of stenoses (vascular occlusions). They have a tubular or hollow cylindrical basic mesh as a body, preferably comprised of webs as supporting elements folded in a zigzag or meandering pattern and running essentially in the circumferential direction as well as webs as connecting struts running in the longitudinal direction and connecting these supporting elements. The basic mesh is open at both ends in the direction of the axis of the hollow cylinder. The tubular basic mesh of such an endoprosthesis is inserted into the blood vessel that is to be treated and serves to support the vessel. Such stents have become established, in particular, for treatment of vascular diseases. Due to the use of stents, constricted areas in the vessels can be widened, resulting in a larger lumen. After insertion of a stent, there is the risk of a restenosis, i.e., reocclusion of the vascular area treated with the stent because of various processes, for example, coagulation of the body fluid in this area due to a change in blood flow or due to an infectious process. To prevent restenoses, such stents are often provided with active pharmaceutical substances which have an anticoagulant effect, for example. With regard to such a stent, it is also desirable for the active pharmaceutical substances to be released in a controlled manner.

Known stents with medication dispensed from a coating may be made of a polymer, for example. Furthermore, depots of medicine with pumps are also already being used. However, one disadvantage of the known approaches is that the active pharmaceutical substances are released continuously and there is no possibility for regulating the release. Furthermore, only a uniform dosage of the substance is implementable and the amount of medicine remaining in the reservoir or depot cannot be determined. The body of the person or animal being treated is burdened by the continuous release of active ingredients.

International Patent Publication No. WO 2004/093643 discloses an implantable device with which a therapeutic substance is delivered by means of a magnetizable implant to a site that is to be treated. To this end, an implant which is implemented as a stent, for example, has a variety of magnetizable properties, i.e., the property of being permanently magnetic. Because of the magnetizable properties of the implant, the therapeutic substance is attracted so the therapeutic substance is arranged in a magnetic carrier. The magnetic carrier is delivered toward the device by the use of a long-range magnetic field. The known approach thus serves to deliver a therapeutic substance that is administered subsequently to a certain predetermined location in the body. The problem of controlling the release of an active pharmaceutical substance over time is inadequately solved in this way because with the known method, the therapeutic substance is delivered from the site of introduction through the body to the site of the implant. This does not allow an accurate prediction of which point in time and in which amount the desired concentration of the therapeutic substance occurs. Furthermore, the side effects that may result from the delivery of the therapeutic substance through the body are still present as in the past. Furthermore, it is often difficult and time-consuming to arrange the therapeutic substances in a suitable magnetic carrier.

U.S. Pat. No. 7,223,282 discloses an implantable device in the form of a stent which has a first and a second material. The first material has a therapeutic substance. The second material which is carried by the stent serves to convert a first type of energy into thermal energy by means of which the therapeutic substance is released from the first material. However, the thermal energy thereby released cannot be controlled accurately, especially with regard to the quantity released, and under some circumstances, e.g., when excessively high temperatures are reached, the thermal energy can damage the tissue of the patient being treated that surrounds the implantable device.

SUMMARY

The present disclosure describes several exemplary embodiments of the present invention.

One aspect of the present disclosure provides an implant, comprising a) a body; b) at least one active pharmaceutical substance; and c) an element which is deflectable in relation to the body and which serves to release the at least one active pharmaceutical substance after or during an external triggering of the deflection.

Another aspect of the present disclosure provides a system, comprising a) a first implant; and b) an excitation device preferably formed as the second implant, whereby the excitation serves to provide external excitation of deflection of the deflectable element of the first implant.

A further aspect of the present disclosure provides a system, comprising a) a first implant having a body and at least one active pharmaceutical substance, wherein the implant has an element which is deflectable in relation to the body and which serves to release the at least one active pharmaceutical substance after or during an external triggering of the deflection; and b) an excitation device preferably formed as the second implant, whereby the excitation serves to provide external excitation of deflection of the deflectable element of the first implant.

One aspect of the present disclosure provides an implant with which it is possible to control the release of an active pharmaceutical substance in a manner that is accurate in terms of quantity and/or time (i.e., with regard to the point in time and/or duration of time) which will not damage the tissue of the patient. A second aspect of the present disclosure creates a system by means of which the desired control of the release of the substance can be achieved.

An implant is described having an element deflectable in relation to the body, serving to release the at least one active pharmaceutical substance during or after an external stimulus of the deflection. For purposes of the present disclosure, the term "deflection" refers to a mechanical displacement of the entire deflectable element or a partial area of the deflectable element in relation to the body of the implant or a part of the body of the implant. On the one hand, the body of the implant may be fixedly connected to the body of the implant at least at a point or along a line (preferably a straight line). For purposes of the present disclosure, the term "deflection" refers to the displacement of a partial area of the deflectable element when the entire deflectable element or its center of gravity is not moved relative to the body of the implant (e.g., in a thickness vibration). Due to the external signal, the at least one active pharmaceutical substance can be released in a targeted manner at a certain point in time and over a desired period of time, triggered by a physician or patient by means of an external device such as the excitation device or by means of a second implant (e.g., by triggering based on time or based on a sensor system present in the external device or in the second implant). For example, the quantity of active pharmaceutical substance dispensed can be controlled here through the controllable amplitude or frequency of the deflection of the deflectable element.

This construction makes is possible to minimize adverse effects for the patient because there is no continuous release of the active pharmaceutical substance. Furthermore, applications of the active pharmaceutical substance that could otherwise be accomplished only by administering injections, e.g., the release of insulin, a hormone treatment (e.g., as part of a contraceptive treatment), in treatment of addictions in which it is desirable for a decreasing dose of the active pharmaceutical substances to be released and in a targeted tumor treatment in oncology or targeted stimulus to induce bone neogenesis by means of an active pharmaceutical substance in orthopedics, can now be achieved through applications of the active pharmaceutical substance. These treatments can thus be implemented for the patients without burdening the patient.

In a preferred exemplary embodiment, the deflection of the deflectable element is a vibration that persists over a predetermined period of time. This deflection can be implemented especially easily. Various vibrations of the deflectable element are conceivable. In the case when the deflectable element is designed as a disk-shaped element or plate, a thickness vibration or a longitudinal vibration may be implemented, for example. In the case of a disk-shaped deflectable element having a cylindrical shape, radial vibrations are also conceivable in addition to vibration in thickness. In the case of a cubical deflectable element, shearing vibrations may also be implemented. In the case of implementation of the deflectable element as a hollow cylindrical element, (wall) thickness vibrations, radial vibrations or longitudinal vibrations in the direction of the longitudinal axis are also conceivable.

In addition, it is preferable if the frequency of the external excitation signal is coordinated with the deflectable element so that the element oscillates at a resonant frequency. Alternatively, the geometry and/or mass of the element may be coordinated with the frequency of the external excitation signal so that the element oscillates at a resonant frequency. This allows control of the release of the substance in an especially simple and targeted manner.

One possibility for implementing such an implant is for the deflectable element to be designed at least partially to be ferromagnetic or permanently magnetic and for the external excitation to be provided by a signal of an alternating magnetic field. Especially preferred frequencies of the alternating magnetic fields are frequencies of approximately 100 Hz to approximately 100 kHz. For example, deflectable elements made of cobalt or iron may be used. It is advantageous here if the body of the implant or other components of the implant do not diminish the alternating magnetic field. The material of the implant must be selected accordingly, preferably the material has an element from the group of paramagnetic metals which have a positive magnetic susceptibility (alkali metals, alkaline earth metals or rare earths). However, an external magnetic exciting field is diminished by the water content of the human or animal body because water is diamagnetic and therefore the release of the active ingredient is restricted. In this case, it would be conceivable if the magnetic excitation field were generated inductively by using a coil in a second implant. The second implant here serves as an excitation device and is set up in the vicinity of the first implant which dispenses the active pharmaceutical substance.

Alternatively, the external excitation may also be accomplished by means of an ultrasonic signal, whereby the ultrasonic signal is coordinated with the deflectable element and the body of the implant so that the deflectable element is deflected in relation to the body of the implant. In particular, frequencies in the range of 30 kHz to 10 MHz may be considered here. However, exactly which frequency is needed will depend on the material and the size of the resonator (deflectable element). The exact required frequency f can be calculated by the formula $f=c/R$, where c is the velocity of sound of the respective material (e.g., steel=5000 m/s, water=1500 m/s) and R denotes the radius of the resonator. Excitation by ultrasound has the advantage that it is not diminished by water. However, very deep regions of the body to be treated cannot be reached by ultrasonic signals.

Excitation by an alternating magnetic field and excitation by ultrasound both allow a targeted release of a medication, because the release of medication can be interrupted when the signal is interrupted. Furthermore, the signal amplitude may also be used to control the release of medication. If the signal is amplified, a larger quantity of active pharmaceutical substance is released. Another advantage that can be achieved by the present invention consists of the fact that the dosage, i.e., the quantity of active pharmaceutical substance released can also be adjusted via the frequency of the alternating magnetic field and/or the ultrasound. Furthermore, it is possible to determine the remaining amount of active pharmaceutical substance in the implant simply by adding up the targeted release amounts. Furthermore, it is possible to place different active pharmaceutical ingredients in or on an implant and to trigger one or more of these substances to be released in a targeted manner, e.g., via a specific excitation frequency for the deflectable element of the respective active ingredient, the frequency optionally being a suitably coordinated resonant frequency.

In a preferred exemplary embodiment that is easy to implement in an inexpensive manner, the implant is designed so that the deflectable element is designed like a plate and preferably has openings. The at least one active pharmaceutical substance can be released through these openings.

In another exemplary embodiment, the deflectable element may also be designed as a layer which is provided with a plurality of deflectable elements. These deflectable elements float in the layer which is provided with the active pharmaceutical substance. Each of the plurality of deflectable elements is preferably designed to be permanently magnetic or ferromagnetic and consequently can be triggered by an alternating magnetic field as the triggering signal. The film is preferably designed to be biodegradable, so that the film can be degraded after consumption of the at least one active pharmaceutical substance. The entire implant may preferably also be designed to be biodegradable.

For purposes of the present disclosure, the term "biodegradation" refers to hydrolytic, enzymatic and other metabolic degradation processes in a living organism which are caused by the body fluids coming in contact with the film or the implant and leading to a gradual dissolution of at least large portions of the film or the implant. The term "biocorrosion" is often used as a synonym for the term biodegradation. For purposes of the present disclosure, the term "bioabsorption" includes the subsequent absorption of the degradation products by the living organism.

Materials suitable for biodegradable films or implants may be of the polymeric or metallic nature, for example. The implant or the film may also consist of multiple materials. The common feature of these materials is their biodegradability. Examples of suitable polymeric compounds include polymers from the group consisting of cellulose, collagen, albumin, casein, polysaccharides (PSAC), polylactide (PLA), poly-L-lactide (PLLA), polyglycol (PGA), poly-D,L-lactide-co-glycolide (PDLLA-PGA), polyhydroxybutyric acid (PHB), polyhydroxyvaleric acid (PHV), polyalkyl carbonates, polyorthoesters, polyethylene terephtalate (PET), polymalonic acid (PML), polyanhydrides, polyphosphazenes, polyamino acids and their copolymers as well as hyaluronic acid. Depending on the desired properties, the polymers may be in pure form, in derivatized form or in the form of blends of copolymers. Biodegradable metallic materials are based on alloys of magnesium, iron, zinc and/or tungsten.

In another preferred exemplary embodiment, the deflectable element is provided in a recess of the body of the implant, whereby the at least one active pharmaceutical substance is also arranged in the recess of the body of the implant, either above or below the element. In this way, an especially simple release of the at least one active pharmaceutical substance may take place. With an active pharmaceutical substance arranged above the deflectable element, the deflection of the element causes the active pharmaceutical substance to be forced outward. With the substance arranged beneath the deflectable element, the substance is delivered to the surface, e.g., through openings in the element, due to the deflection of the element.

The deflectable element especially preferably has continuous openings which are closed in the condition without external excitation and are at least partially open in the condition with external excitation and therefore the openings release the at least one active pharmaceutical substance. The opening and closing of the through-openings may be accomplished, for example, by a thickness vibration of the deflectable element. In the unexcited state, the deflectable element is in the form of a plate with continuous openings on an area of the body of the implant. In this way, the openings of the deflectable element which is designed as a plate are closed. In excitation, the deflectable element executes thickness vibrations so that the plate-shaped deflectable element is temporarily raised by the area of the body of the implant that closes the openings thereby causing a release of the at least one active pharmaceutical substance.

Another exemplary embodiment of the implant of the present disclosure has the deflectable element arranged in a through-opening passing through the body of the implant, closed on one side by a permeable membrane and on the other side by an impermeable plastic cover, whereby the deflectable element and the at least one active pharmaceutical substance are provided in the opening between the semipermeable membrane and the plastic cover. With this exemplary embodiment it is possible to fill the opening with the active pharmaceutical substance in a simple manner before insertion of the implant.

In a preferred exemplary embodiment, the semipermeable membrane has a pore size of approximately 0.5 µm to approximately 1 µm (depending on the particle size of the substance used). This pore size is advantageous because, on the one hand, little diffusion occurs with these pore sizes and, on the other hand, the pore size makes it possible to expel the molecule of active ingredient.

The aspect described above is also achieved by a system comprising an inventive implant which is the first implant described above and an excitation device such that the excitation device serves to provide external excitation of the deflection of the deflectable element of the first implant. The excitation device is preferably designed as a second implant which is arranged in the immediate vicinity, i.e., at most at a distance between approximately 5 cm and approximately 10 cm away from the first implant in a preferred manner. In this way, the excitation may be accomplished in a more targeted manner and the excitation signal is diminished to a lesser extent so that the release of the active pharmaceutical substance is less subject to error.

In a preferred exemplary embodiment, the excitation device creates an alternating magnetic field or an ultrasonic signal for excitation. By means of these excitation forms, an especially simple, inexpensive and easy-to-control excitation is possible.

To avoid diminishing the alternating magnetic field due to the water incorporated in the body to be treated, the alternating magnetic field is generated by the excitation device by excitation via an external induction coil.

In an especially preferred exemplary embodiment, the excitation device has a sensor unit with which at least one bodily function is measured, whereby the excitation device is designed, so that an excitation signal is delivered only when at least one of the at least one measured bodily functions is within a predetermined range. Release of the active pharmaceutical substance may be accomplished in a more targeted manner in this way.

As an alternative to the possibility of generating a permanent excitation of the deflectable element, e.g., at the resonant frequency, ultrasonic pulses or magnetic pulses with a high amplitude may be used, optionally repeatedly, for excitation of the deflectable element.

BRIEF DESCRIPTION OF THE DRAWINGS

Various aspects of the present disclosure are described hereinbelow with reference to the accompanying figures.

All the features described and/or illustrated herein constitute subject matter of the present disclosure, regardless of how they are combined in the claims or their reference back to previous claims.

FIG. 1a shows a schematic diagram of thickness oscillation vibration which the deflectable element of an inventive implant can execute, depending on the design of the deflectable element;

FIG. 1b shows a schematic diagram of radial direction oscillation vibration which the deflectable element of an inventive implant can execute, depending on the design of the deflectable element;

FIG. 1c shows a schematic diagram of shear force direction oscillation vibration which the deflectable element of an inventive implant can execute, depending on the design of the deflectable element;

FIG. 1d shows a schematic diagram of wall thickness direction oscillation vibration which the deflectable element of an inventive implant can execute, depending on the design of the deflectable element;

DETAILED DESCRIPTION

Figure 2:
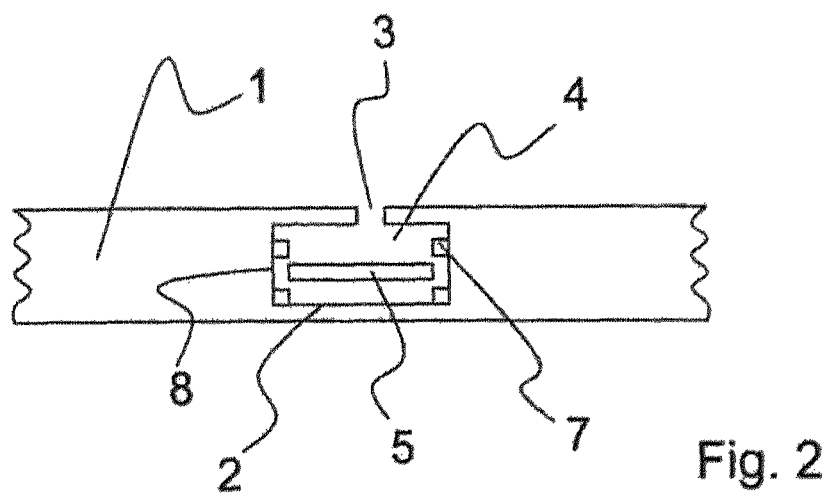
FIG. 2 shows a cross-section view of a first exemplary embodiment of an inventive implant.

FIG. 1 shows various possible exemplary implementations of a deflectable element of an inventive implant. FIG. 1a) shows a plate-shaped deflectable element 5 with a square plate area. A rectangular plate area is also conceivable. FIG. 1b) shows a disk-shaped deflectable element 35, which is designed essentially as a circular disk, but the embodiment of an elliptical disk is also conceivable. A cuboid deflectable element 45 is shown in FIG. 1c). FIG. 1d) shows a hollow cylindrical deflectable element 55. In FIGS. 1a) through 1d), the vibrations excitable by the excitation signal are illustrated by arrows next to the deflectable elements 5, 35, 45 and 55. The plate-shaped excitable element 5 shown in FIG. 1a) may consequently execute thickness vibrations and longitudinal vibrations. The disk-shaped deflectable element 35 shown in FIG. 1b) can execute radial vibrations and thickness vibrations. Shearing vibrations are possible with the cuboid deflectable element 45. Thickness vibrations (of the wall), radial vibrations and longitudinal vibrations can be performed by the hollow cylindrical deflectable element 55. The x-, y- and z-axes of the deflectable elements 5, 35, 45 and 55 are labeled as A1, A2 and A3, respectively.

Exemplary embodiments of the implant of the present disclosure are explained in greater detail hereinbelow on the basis of transverse sections of a stent. It is self-evident that the structure of the release unit of the respective stent as shown here comprising an element in which the active pharmaceutical substance is arranged and deflectable element may also be integrated into other implants.

The implant of the present disclosure may be designed as a stent, for example, in whose basic lattice as the body of the stent one or more active pharmaceutical substances are arranged, i.e., in or on its webs of the supporting elements or connecting struts.

The body of such an inventive stent preferably consists of a metallic material of one or more metals from the group consisting of iron, magnesium, nickel, tungsten, titanium, zirconium, niobium, tantalum, zinc and silicon and, optionally, a second component of one or more metals from the group consisting of lithium, sodium, potassium, calcium and manganese, preferably a zinc-calcium alloy. In another exemplary embodiment, the base body consists of a shape-memory material of one or more materials from the group consisting of nickel-titanium alloys and copper-zinc-aluminum alloys, preferably nitinol. In another preferred exemplary embodiment, the base body of the stent is made of stainless steel, preferably a Cr—Ni—Fe steel, preferably the 316L alloy, or a Co—Cr steel. Furthermore, the basic lattice 2 may consist at least partially of plastic and/or a ceramic.

In another exemplary embodiment, the basic lattice consists of an absorbable magnesium alloy having the following composition and ranges of components:

rare earths 2.0 to 30.0 wt %,
    yttrium 2.0 to 20.0 wt %,
    zirconium 0.3 to 5.0 wt %,
    remainder 0 to 10.0 wt % (optionally neodymium, for example), where magnesium (at least 60.0 wt %) accounts for the remaining amount of the alloy by weight, up to a total of 100 wt %.

FIG. 2 shows a cross section view through a body section, i.e., a strut 1 of a stent. A recess 2 which has an opening 3 on one side of the strut is arranged in the strut 1. In another exemplary embodiment, multiple openings 3 may also be provided. One or more active pharmaceutical substances 4 are arranged in the recess 2. Furthermore, the recess 2 has a plate-shaped deflectable element 5, which is arranged with its two opposing ends loosely between step-shaped protrusions 7 on the side wall 8 of the recess 2, the protrusions arranged above and below the element 5. By means of external ultrasonic excitation, the plate-shaped deflectable element 5 can be set in vibration. Preferably, the intrinsic frequency of the deflectable element 5 is excited here so that it vibrates with a resonant frequency. Due to the vibration of the deflectable element 5, preferably in a direction perpendicular to the surface of the plate 5, the active pharmaceutical substance 4 arranged above it in the recess 2 is released through the opening 3 into the body, i.e., in the case of the stent, the active pharmaceutical substance 4 is released into the body fluid in the vessel in which the stent is arranged. The thickness of the stent strut 1 preferably amounts to approximately 1 mm.

Figure 3:
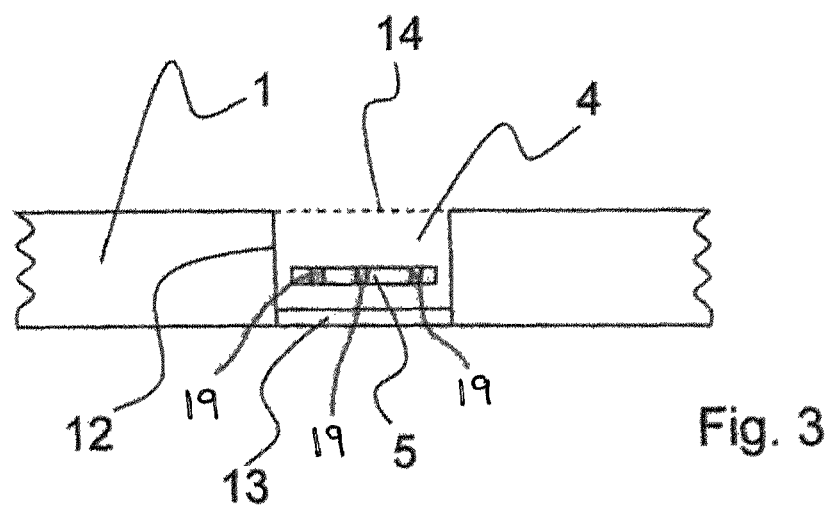
FIG. 3 shows a cross section view of a second exemplary embodiment of an inventive implant.

In the exemplary embodiment depicted in FIG. 3, the stent strut 1 has a through-opening 12 which has a cylindrical shape, for example. This opening 12 is closed on one end by an impermeable cap 13 made of a polymer material. A plate-shaped or circular disk-shaped deflectable element 5 is arranged above this cap in the through-opening. Above the plate-shaped deflectable element 5 there are one or more active pharmaceutical substances 4 and, for closing the opening 12 on the end opposite the cap 13, a semipermeable membrane 14. The plate-shaped deflectable element 5 may be excited either by ultrasound or by means of an alternating magnetic field, if the deflectable element is designed to be at least partially ferromagnetic or permanently magnetic. In this way, the plate-shaped deflectable element is set in vibration, inducing the release of the active pharmaceutical substance(s) through the semipermeable membrane 14. Through such an exemplary embodiment, stent struts with a thickness of approximately 100 µm can be furnished with one or more active pharmaceutical substances 4, which can be released in a targeted manner. In addition, simple filling of the opening 12 with the active pharmaceutical substance(s) 4 is also possible.

Figure 4:
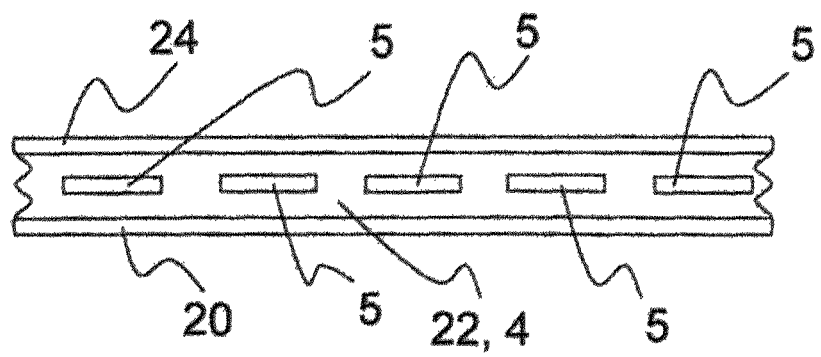
FIG. 4 shows a cross section view of a third exemplary embodiment of an inventive implant.

In a further exemplary embodiment of the design illustrated in FIG. 3, the wall of a stent body may also be designed so that the wall consists of a permeable or nonpermeable carrier layer 20, as illustrated in FIG. 4, an intermediate layer 22, which is arranged in between and is provided with one or more active pharmaceutical substances 4, and a permeable cover layer 24. A plurality of deflectable elements 5 arranged in the intermediate layer 22 may be designed to be ferromagnetic and/or permanently magnetic. These elements 5 are preferably designed like plates and are arranged side-by-side so the elements float in the liquid or gelatinous intermediate layer 22. If an active pharmaceutical substance is arranged above or below each element 5, the substance may be released through the semipermeable cover layer 24 during and after excitation of the corresponding element 5 (i.e., as the signal and/or the deflection subsides). If the carrier layer 20 is designed to be permeable, then the substance may also be released through this layer. The elements arranged side-by-side may be provided with different active pharmaceutical substances, e.g., in individual chambers present in the intermediate layer 22, so that they can be excited specifically with different excitation signals with corresponding supply of the excitation signal and/or corresponding design of the elements 5, so that the respective active pharmaceutical substance is released in a specific manner.

Figure 5:
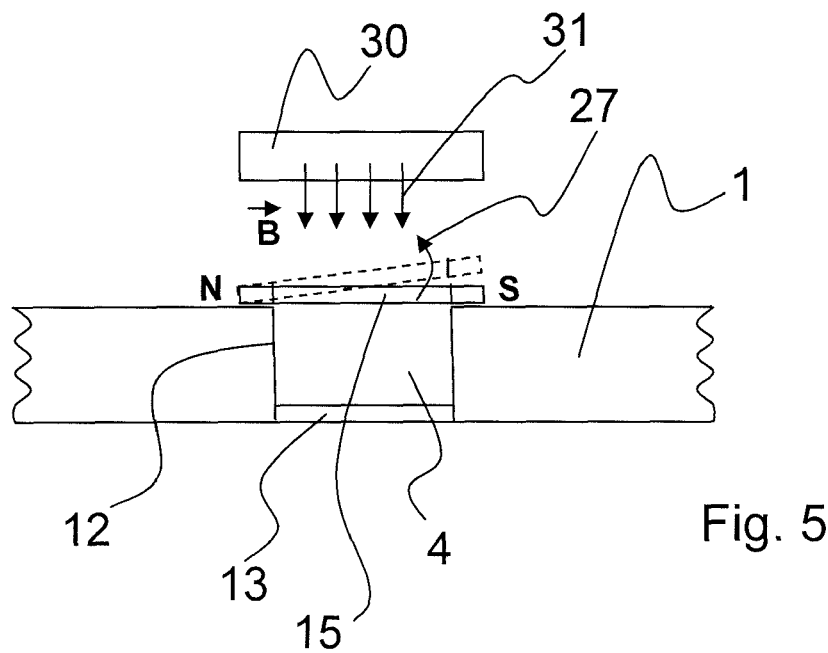
FIG. 5 shows a cross section view of a third exemplary embodiment of an inventive implant with a schematic diagram of an excitation device.

The exemplary embodiment of the implant according to the present disclosure depicted in FIG. 5 has a through-opening 12 which is closed on one side with a cap 13 and is covered on the other side with a plate-shaped deflectable element 15. This element 15 is magnetized. The magnetic poles are labeled with the letters "N" and "S" in FIG. 5. As FIG. 5 shows, the magnetization is such that one magnetic pole (N or S) is arranged at each end of the plate-shaped element 15. One of these poles (N or S) is movably attached (like a hinge) to the strut (pole N in the exemplary embodiment shown here). On excitation with an excitation device, which has an electromagnetic coil 30 in the exemplary embodiment shown in FIG. 5, either the magnetic south pole S of the first end of the plate-shaped element 15 (see FIG. 5) is attracted more strongly by the coil 30 (see FIG. 5), or in another exemplary embodiment (not shown here) the magnetic north pole N of the plate-shaped element 15 is attracted more strongly, depending on the position of the magnetic field 31 generated by the coil 30 (magnetic positive pole with a magnetic flux density B). Thus in the exemplary embodiment depicted in FIG. 5, on excitation of the south pole S, the magnetic plate is raised. On excitation of the magnetic north pole N, the plate remains closed. The movement of the element 15 is illustrated by the arrow 27 in FIG. 5. The deflectable element 15 is raised here on one side (see plate shown with broken lines). Due to this deflection of the element 15, active pharmaceutical substance 4 arranged in the opening 12 can escape. The principle illustrated on the basis of FIG. 5 corresponds to the principal of a "reed relay" and/or a "reed contact." After shutting down or reversing (reversing the polarity) of the magnetic field of the coil 30, the plate-shaped element 15 returns back to its starting position. This movement of the plate 15 can be repeated several times in succession. In a preferred exemplary embodiment, the plate-shaped element 15 as well as the coil 30 (magnet) are arranged so they are not far from one another in the body. The distance between the plate-shaped element 15 and the coil 30 should preferably amount to a maximum of approximately 5 cm. The coil 30 may either generate a magnetic field with a certain preset frequency or as an alternative may be designed to be controllable from the outside.

Deflections of the deflectable elements 5, 15, 35, 45, 55 described above amount to a few nanometers up to a few micrometers.

Figure 6:
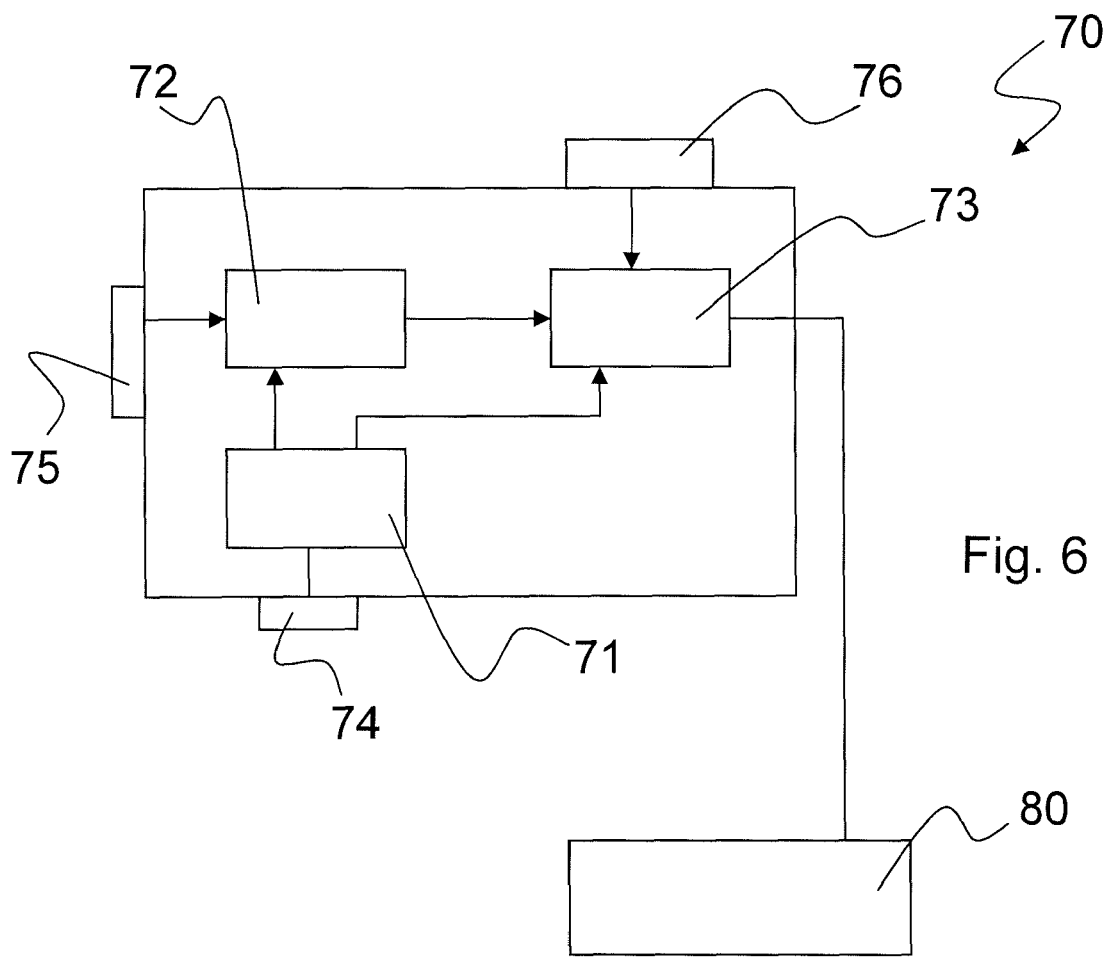
FIG. 6 shows a schematic diagram of an exemplary excitation device.

FIG. 6 shows an exemplary embodiment of an excitation device 70 as a power pack part 71 with a rectifier, an adjustable frequency sine-wave generator 72 and an amplifier output stage 73. These elements of the excitation device 70 are electrically connected to one another. The excitation device 70 also has a power supply connection 74 which is connected to the power supply unit 41. The frequency required for excitation of the deflectable element is adjusted by means of an operating element 45 designed as a turn knob, for example, for adjusting the frequency generated by the frequency sine-wave generator 42. The amplitude of the current and/or voltage can be adjusted by the additional operating element 46, which preferably includes one operating knob or several operating knobs. The additional operating element 46 is connected to the amplifier output stage 43, whereby a current and/or voltage of the amplitude set by the operator is generated by means of the amplifier output stage 43.

Still referring to FIG. 3, openings 19 may be disposed through the deflectable element 5. The openings 19 are closed in a condition where no external excitation is provided to the deflectable element 5 and the openings 19 are at least partially open in a condition where external excitation is provided to the deflectable element 5. If active pharmaceutical substance 4 is located below the deflectable element 5 (opposite the membrane 14 or an opening, such as opening 3 in FIG. 2) and external excitation is provided to the deflectable element 5, the openings open and close to release the active pharmaceutical substance 4.

The amplifier output stage 73 is preferably connected electrically by cable to the probe 80 which is used for external excitation of the respective deflectable element and is part of the excitation device 70. In the exemplary embodiment shown in FIG. 6, the probe 80 is arranged separately and is movable by the other components of the excitation device 70.

For excitation by means of an alternating magnetic field, the probe 80 preferably has a coil made of copper wire which is arranged on a soft iron core. In another exemplary embodiment, the probe 80 is designed for excitation by an alternating magnetic field or for excitation by ultrasound in addition or as an alternative to excitation by an alternating magnetic field; and the probe, therefore, contains a piezoelectric crystal which is connected to a mechanical coupling element which extends up to at least a surface of the probe 80.

In the case of excitation by means of an alternating magnetic field, after adjusting the frequency and amplitude parameters, the probe 80 is positioned by means of the operating elements 75 and 76 at a short distance (e.g., approximately 5 cm to 10 cm) away from the patient who is supine on a table, for example, for excitation of the deflectable element to release the active pharmaceutical substance. Then the deflectable element of the implant, which is implanted in the patient's body, is excited by means of the alternating magnetic field.

In the case of excitation by ultrasound, the probe 80 is placed on the patient's body after adjusting the parameters on the excitation device 70. First a gel is applied to the location where the probe 80 is to be placed, so that the mechanical coupling element of the probe 80 is connected to the patient's body via the gel. Then the implant, which is implanted in the patient's body, is excited by means of ultrasound via the excitation device 70 so that the active pharmaceutical substance is released by deflection of the deflectable element.

All patents, patent applications and publications referred to herein are incorporated by reference in their entirety.

What is claimed is:

1. An implant, comprising:
  a) a body;
  b) at least one recess formed in the body, the recess adapted to retain at least one active pharmaceutical substance;
  each of the at least one recesses having:
  an opening providing access to the at least one recess; and
  a deflectable element having an upper surface portion and a lower surface portion and disposed within the at least one recess such that the at least one pharmaceutical substance is in contact with either or both the upper and lower surfaces of the deflectable element when the level of pharmaceutical substance is at its maximum, the deflectable element being at least partially either ferromagnetic or permanently magnetic, the deflectable element being displaceable by vibration in response to an excitation signal from a resting first state which does not allow the at least one pharmaceutical substance to move from the at least one recess through the opening, to a vibrating second state, the vibrating second state causing agitation of the at least one active pharmaceutical substance from the at least one recess through the opening or movement of the at least one active pharmaceutical substance from the at least one recess through the opening, wherein in response to the removal of the excitation signal the deflectable element returns to the resting first state which can thereafter again be excited into the vibrating second state.

2. The implant of claim 1, wherein each deflectable element is repeatedly cyclable between the resting first state and excited second state in response to the application or nonapplication of the excitation signal.

3. The implant of claim 1, wherein a frequency of an external excitation signal is coordinated with the deflectable element so that the vibration of the deflectable element is at a resonant frequency.

4. The implant of claim 1, wherein a geometry or a mass of the deflectable element is coordinated with a frequency of an external excitation signal, so that vibration of the deflectable element is at a resonant frequency.

5. The implant of claim 1, wherein an external excitation takes place by means of a signal of an alternating magnetic field.

6. The implant of claim 1, wherein the deflectable element is plate-shaped and has at least one opening.

7. The implant of claim 1, wherein the body includes a layer that comprises a degradable film.

8. The implant of claim 1, wherein the deflectable element is provided in a recess in the body, whereby the at least one active pharmaceutical substance is arranged above or below the deflectable element.

9. The implant of claim 8, wherein the deflectable element has openings which are closed in a state without external excitation and are temporarily open in a state with external excitation and thereby release the at least one active pharmaceutical substance.

10. The implant of claim 8, wherein the deflectable element is arranged in an opening passing through the body, the opening being closed on one side by a semipermeable membrane and closed on another side by an impermeable plastic cover, whereby the deflectable element and the at least one active pharmaceutical substance are provided between the semipermeable membrane and the plastic cover in the opening.

11. The implant of claim 10, wherein the semipermeable membrane has a pore size between approximately 0.5 µm and approximately 1 µm.

* * * * *